United States Patent [19]

Burk

[11] Patent Number: 5,906,989
[45] Date of Patent: May 25, 1999

[54] CYCLOPENTANE(ENE) HEPTENOIC OR HEPTANOIC ACIDS AND DERIVATIVES THEREOF USEFUL AS THERAPEUTIC AGENTS

[75] Inventor: Robert M. Burk, Laguna Beach, Calif.

[73] Assignee: Allergan Sales, Inc., Irvine, Calif.

[21] Appl. No.: 09/084,805

[22] Filed: May 26, 1998

Related U.S. Application Data

[62] Division of application No. 08/861,414, May 21, 1997, Pat. No. 5,798,378, which is a division of application No. 08/740,883, Nov. 4, 1996, Pat. No. 5,681,848, which is a division of application No. 08/445,842, Jul. 11, 1995, Pat. No. 5,587,391, which is a division of application No. 08/174,535, Dec. 28, 1993, Pat. No. 5,545,665.

[51] Int. Cl.$^6$ ............... A61K 31/44; A61K 31/505; C07D 211/70; C07D 209/04
[52] U.S. Cl. ............... 514/357; 514/277; 514/471; 514/461; 514/530; 514/532; 514/561; 514/570; 514/646; 546/329; 546/334; 546/339; 546/340; 546/341; 549/491; 549/496
[58] Field of Search ............... 546/329, 334, 546/339–341; 514/357, 277, 471, 461, 530, 532, 561, 570, 646; 549/491, 496

[56] References Cited

U.S. PATENT DOCUMENTS

| | | | |
|---|---|---|---|
| 3,845,115 | 10/1974 | Lincoln, Jr. et al. | 562/503 |
| 3,847,967 | 11/1974 | Lincoln, Jr. et al. | 560/121 |
| 3,853,950 | 12/1974 | Lincoln et al. | 560/121 |
| 3,931,206 | 1/1976 | Bowler et al. | 546/302 |
| 4,088,779 | 5/1978 | Vlattas | 514/473 |
| 4,235,930 | 11/1980 | Skuballa et al. | 514/63 |
| 4,256,745 | 3/1981 | Skuballa et al. | 514/239.2 |
| 4,338,316 | 7/1982 | Marsham | 514/247 |
| 4,351,846 | 9/1982 | Matsumoto et al. | 514/530 |
| 4,359,467 | 11/1982 | Vorbruggen et al. | 514/63 |
| 4,403,100 | 9/1983 | Morton, Jr. | 560/121 |
| 4,447,428 | 5/1994 | Collington et al. | 210/635 |
| 4,494,274 | 1/1985 | Thurlow | 16/110 A |
| 4,560,786 | 12/1985 | Skuballa et al. | 560/55 |
| 4,562,207 | 12/1985 | Imaki et al. | 514/573 |
| 4,599,353 | 7/1986 | Bito | 514/573 |
| 5,004,752 | 4/1991 | Raduechel et al. | 514/530 |
| 5,006,539 | 4/1991 | Jones et al. | 514/357 |
| 5,034,413 | 7/1991 | Chan, II et al. | 514/530 |
| 5,238,961 | 8/1993 | Woodward et al. | 514/573 |
| 5,270,049 | 12/1993 | Chan, II et al. | 514/530 |
| 5,352,708 | 10/1994 | Woodward et al. | 514/729 |
| 5,376,683 | 12/1994 | Klar et al. | 514/530 |
| 5,414,016 | 5/1995 | Skuballa et al. | 514/460 |
| 5,422,368 | 6/1995 | Sternschantz et al. | 514/530 |

FOREIGN PATENT DOCUMENTS 0364417  4/1990  European Pat. Off. .

OTHER PUBLICATIONS

Starr, M.S., *Exp. Eye Res.* 1971, 11, pp. 170–177.
Bito, L.Z. *Biological Protection with Prostaglandins*, Cohen, M.M., ed., Boca Raton, Fla, CRC Pres Inc., 1995, pp. 231–252.
Bito, L.Z. *Applied Pharmacology in the Medical Treatment of Glacoma*, Drance, S.M. & Neufeld, A.H. eds., New York, Brune & Stratton, 1984, pp. 477–505.
Nilsson et al, *Inv. Ophthalmol. Vis. Sci.* 28 (suppl), 1987, pp. 284.
Bito, L.Z., *Arch Ophthalmol.* 105, 1987, 1036.
Siebold et al, *Prodrug*, 5, 1987, 3.

Primary Examiner—Deborah C. Lambkin
Attorney, Agent, or Firm—Robert J. Baran; Martin A. Voet; Carlos A. Fisher

[57] ABSTRACT

The invention relates to 7-[5-hydroxy-2-(hydroxyhydrocarbyl or heteroatom-substituted hydroxy hydrocarbyl)-3-hydroxy-cyclopentyl(enyl)] heptanoic or heptenoic acids and derivatives of said acids, wherein one or more of said hydroxy groups are replaced by an ether group. The compounds of the present invention are potent ocular hypotensives, and are particularly suitable for the management of glaucoma.

22 Claims, 4 Drawing Sheets

CYCLOPENTANE(ENE) HEPTENOIC OR HEPTANOIC ACIDS AND DERIVATIVES THEREOF USEFUL AS THERAPEUTIC AGENTS

CROSS REFERENCE TO RELATED APPLICATIONS

This patent application is a divisional of U.S. Ser. No. 08/861,414 filed May 21, 1997, now U.S. Pat. No. 5,798,388; which is a divisional of patent application U.S. Ser. No. 08/740,883 filed Nov. 4, 1996, now U.S. Pat. No. 5,681,848 issued Oct. 28, 1997; which is a divisional of patent application U.S. Ser. No. 08/445,842 filed on Jul. 11, 1995, now U.S. Pat. No. 5,587,391 issued Dec. 24, 1996; which is a divisional of U.S. Ser. No. 08/174,535 filed on Dec. 28, 1993, now U.S. Pat. No. 5,545,665 issued Aug. 13, 1996.

FIELD OF THE INVENTION

The present invention provides 7-[5-hydroxy-2-(hydroxyhydrocarbyl or heteroatom-substituted hydroxyhydrocarbyl)-3-hydroxycyclopentyl(enyl)] heptanoic or heptenoic acids and amine, amide, ether, ester and alcohol derivatives of said acids, wherein one or more of said hydroxy groups are replaced by an ether group. The compounds of this invention are potent ocular hypotensives, and are particularly suitable for the management of glaucoma. Moreover, the compounds of this invention are smooth muscle relaxants with broad application in systemic hypertensive and pulmonary diseases; with additional application in gastrointestinal disease, reproduction, fertility, incontinence, shock, inflammation, immune regulation, disorders of bone metabolism, renal dysfunction, cancer and other hypoproliferative diseases.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170–177; Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_1$, $PGE_2$, and certain lipid-soluble esters such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28 (suppl), 284 (1987)].

The isopropyl ester of $PGF_2\alpha$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending U.S. patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl,11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15- 9,15- and 9,11-diesters of prostaglandins, for example 11,15-dipivaloyl PGF$_{2\alpha}$ are known to have ocular hypotensive activity. See the co-pending patent applications U.S. Ser. No. 385,645 filed 27 Jul. 1990, now U.S. Pat. No. 4,494,274; 584,370 which is a continuation of U.S. Ser. Nos. 386,312, and 585,284, now U.S. Pat. No. 5,034,413 which is a continuation of U.S. Ser. No. 386,834, where the parent applications were filed on 27 Jul. 1989. The disclosures of these patent applications are hereby expressly incorporated by reference.

SUMMARY OF THE INVENTION

We have found that certain 7-[5-hydroxy-2-(hydroxyhydrocarbyl or heteroatom-substituted hydroxyhydrocarbyl)-3-hydroxycyclopentyl(enyl)] heptanoic or heptenoic acids and amine, amide, ether, ester and alcohol derivatives of said acids, wherein one or more of said hydroxy groups are replaced by an ether group are potent ocular hypotensive agents. We have further found that such compounds may be significantly more potent than their respective parent compounds and, in the case of glaucoma surprisingly, cause no or significantly lower ocular surface hyperemia than the parent compounds.

The present invention relates to methods of treating cardiovascular, pulmonary-respiratory; gastrointestinal, reproductive, allergic disease, shock and ocular hypertension which comprises administering an effective amount of a compound represented by the formula I

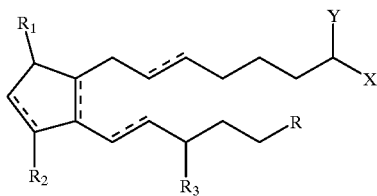

wherein either the cyclopentane radical or the α or ω chain may be unsaturated; R is a hydrocarbyl radical or a heteroatom substituted hydrocarbyl radical comprising up to ten carbon atoms and one or more of the hydrogen or carbon radicals in said hydrocarbyl radical may be substituted with oxygen, sulfur, nitrogen, phosphorus or halogen, e.g. chloro and fluoro; $R_1$, $R_2$ and $R_3$ are selected from the group consisting of hydroxy, hydrocarbyloxy and heteroatom substituted hydrocarbyloxy wherein said hydrocarbyl radical comprises up to 20, e.g. 10 carbon atoms; Y represents 2 hydrogen radicals or an oxo radical and X represents a hydroxyl, a hydrocarbylcarboxy, a hydrocarbyloxy, amino or mono or dialkyl amino radical; provided, however, at least one of $R_1$, $R_2$ and $R_3$ is a hydrocarbyloxy or heteroatom substituted hydrocarbyloxy, i.e., an ether group and preferably only one of $R_1$, $R_2$ and $R_3$, is an ether group, or a pharmaceutically-salt thereof.

Preferably R, $R_1$, $R_2$ and $R_3$ are selected from the group consisting of alkyl, alkenyl or aryl radicals and heteroatom-substituted derivatives thereof wherein the heteroatoms are as defined above and said radicals have up to 10 carbon atoms. Said heteroatom-substituted derivatives may include halo, e.g. fluoro, chloro, etc., nitro, amino, thiol, hydroxy, alkyloxy, alkylcarboxyl radicals. Examples of suitable R, $R_1$, $R_2$, and $R_3$ radicals are methyl, ethyl, propyl, butyl, propenyl, cyclopentyl, cyclohexyl, phenyl, thienyl, furanyl, pyridyl, etc.

Most preferably, $R_1$, $R_2$ and $R_3$ are selected from the group consisting of hydroxy and alkyloxy or alkenyloxy radicals having up to 7 carbon atoms.

More preferably the method of the present invention comprises administering a compound represented by the formula II

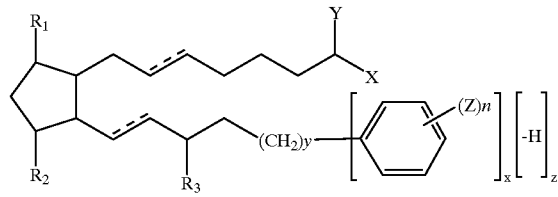

wherein y is 0 or 1 to 5, Z is a radical selected from the group consisting of halo, e.g. fluoro, chloro, etc., nitro, amino, thiol, hydroxy, alkyloxy, alkylcarboxy, etc. and n is 0 or an integer of from 1 to 3, x and z are 0 or 1, and when x is 0, z is 1 and when z is 0, x is 1 and the symbols $R_1$, $R_2$, $R_3$, and Y are as defined above.

Preferably the compound used in the above method of treatment is a compound of formulas (III or IV).

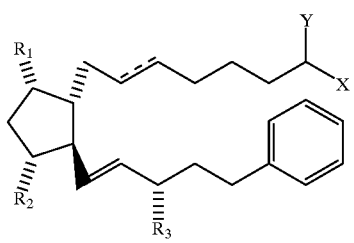

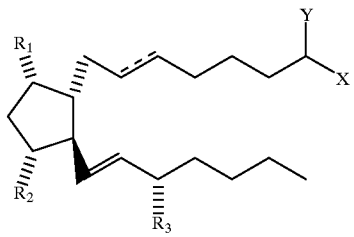

wherein $R_1$, $R_2$, $R_3$, X and Y are as defined above and the hatched and triangular lines are defined below.

In a further aspect, the present invention relates to pharmaceutical compositions comprising a therapeutically effective amount of a compound of formulae (I), (II), (III), or (IV) wherein the symbols have the above meanings, or a pharmaceutically acceptable salt thereof in admixture with a non-toxic, pharmaceutically acceptable liquid vehicle.

In a still further aspect, the present invention relates to certain novel 7-[5-hydroxy-2-(hydroxyhydrocarbyl or hydroxyheteroatom-substituted hydrocarbyl)-3-hydroxycyclopentyl(enyl)] heptanoic or heptenoic acids and amine, amide, ether, ester and alcohol derivatives of said acids, wherein one or more of said hydroxy groups are replaced by an ether group or a pharmaceutically acceptable salt of such compounds.

BRIEF DESCRIPTION OF THE DRAWINGS FIGURES

DETAILED DESCRIPTION OF THE INVENTION

In all of the above formulae the dotted lines on bonds between carbons 5 and 6 (C-5) of the a chain, between carbons 13 and 14 (C-13,) of the w chain, and between carbons 10 and 11 (C-11) of the cyclopentane ring, indicate a single or a double bond which can be in the cis or trans configuration (Of course, the C-10 and C-11 double bonds being part of the cyclopentane ring will exist only as cis double bonds). If two solid lines are used that indicates a specific configuration for that double bond. Hatched lines at positions C-8, C-9, C-11, C-12 and C-15 indicate the a configuration. If one were to draw the b configuration, a solid triangular line would be used.

In the compounds used in accordance with the present invention, compounds having the C-8, C-9, C-11, C-12 or C-15 substituents in the a or b configuration are contemplated.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "hydrocarbyl" means radicals having up to 20 carbon atoms and the remaining atoms comprising said hydrocarbyl radical are hydrogen. In the "heteroatom-substituted" radicals any of the carbon atoms or the hydrogen atoms may be replaced by one of the above defined heteroatoms. Such hydrocarbyl radicals include aryl, alkyl, alkenyl and alkynyl groups of appropriate lengths, and may be methyl, ethyl, propyl, butyl, pentyl, or hexyl, or an isomeric form thereof; ethenyl, propenyl, etc.; phenyl, etc.

Figure 1:
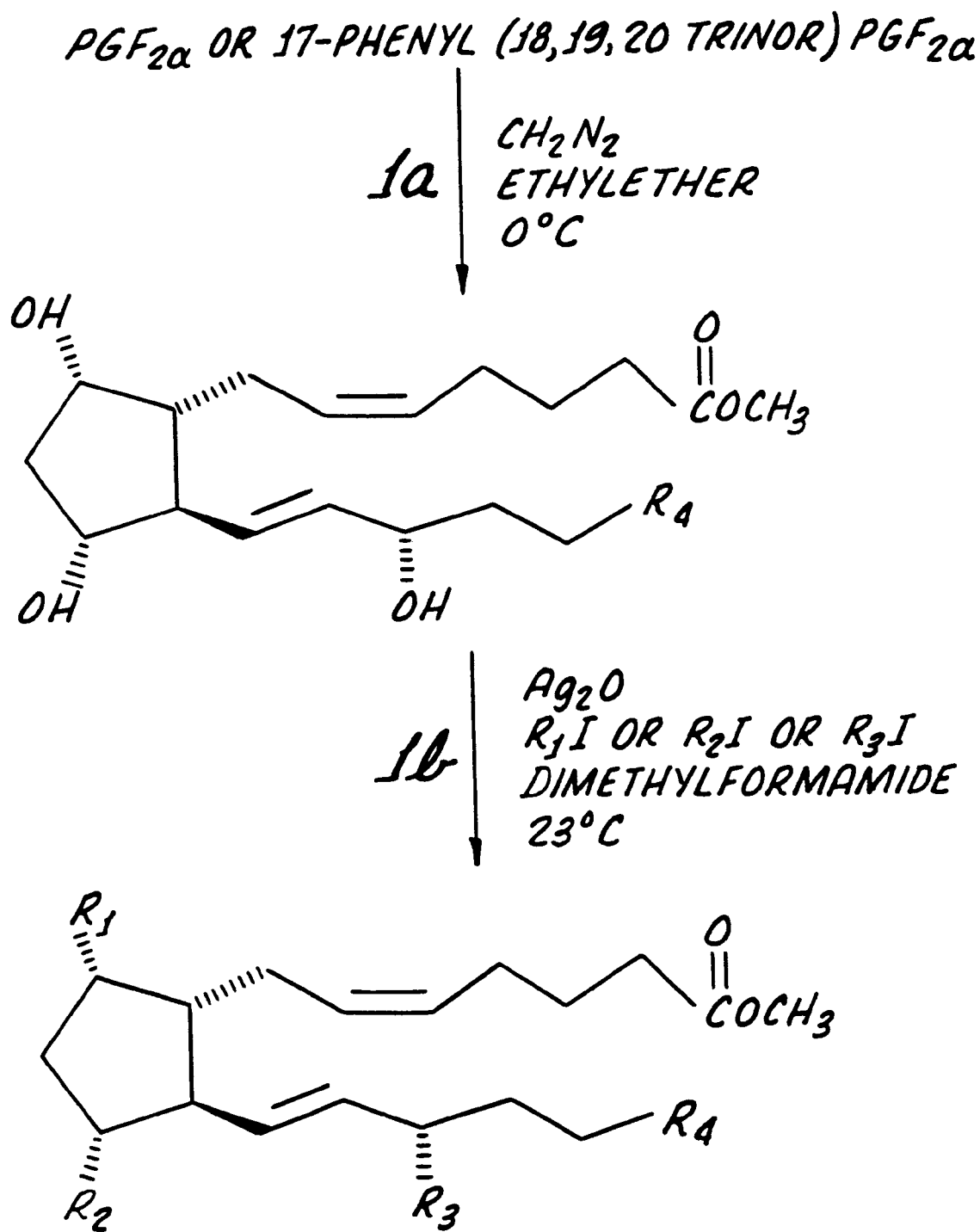
FIG. 1 is a schematic representation of the synthesis of the ethers of this invention, i.e., the 9; 11; 15; 9, 11; 9, 15; 11, 15 ethers, etc.

In FIG. 1 PGF$_{2a}$ or 17-phenyl (18, 19, 20 trinor) PGF2a is reacted with diazomethane to convert such compounds to the corresponding 1-methyl ester. In this scheme R$_4$ is n-propyl or phenyl. Subsequently, as shown in Reaction 1b and further illustrated in Examples 1 and 3, the above 1-methyl esters are reacted with an organoiodide, represented by R$_1$I, R$_2$I or R$_3$I, in the presence of Ag$_2$O and dimethyl formamide, e.g. at 23° C.

Figure 2:
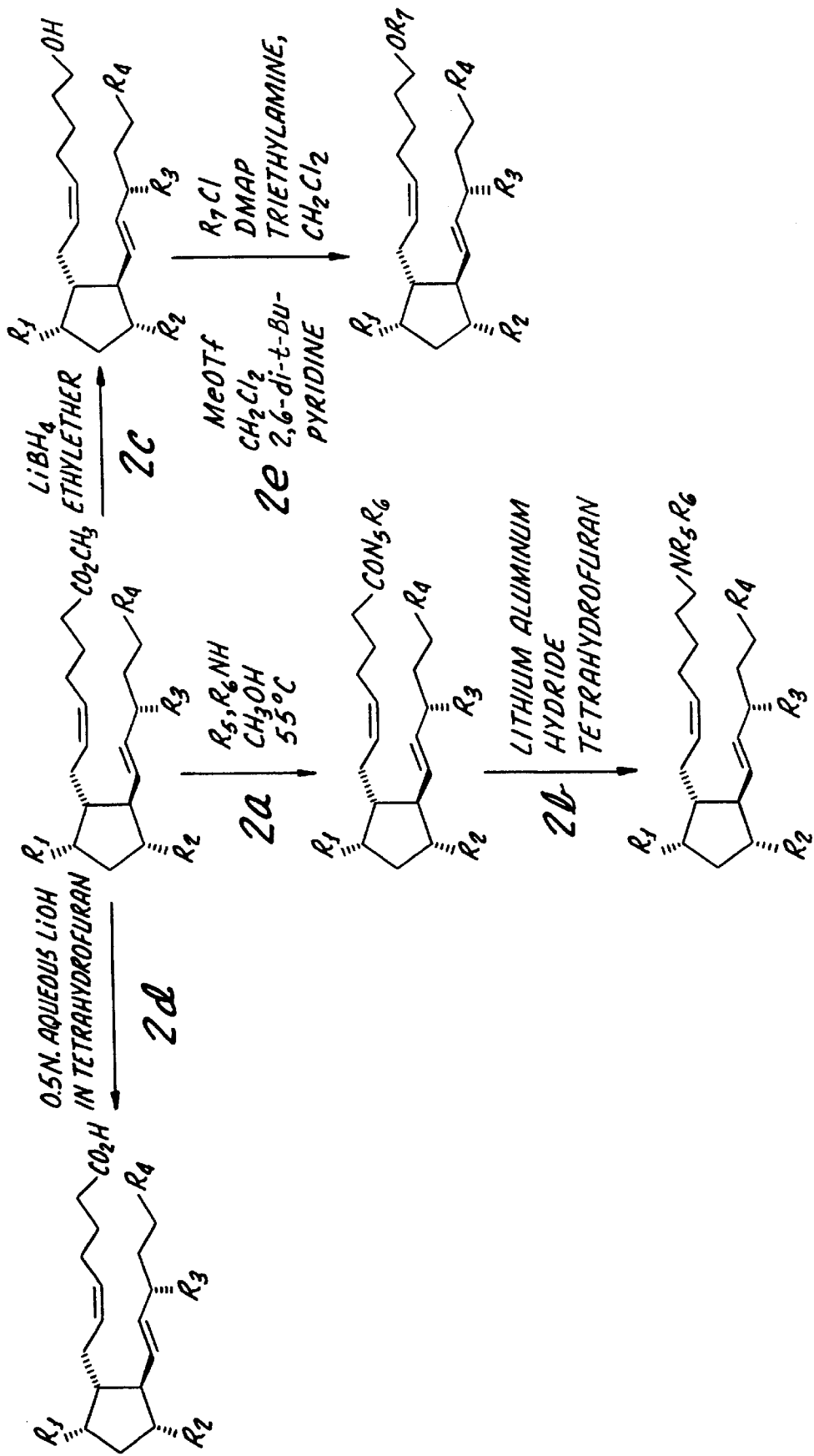
FIG. 2 is a schematic representation of the synthesis of various other compounds of the invention from said 9, 11 and/or 9,15 ethers of FIG. 1.

In FIG. 2 the 1-methyl ester, prepared according to the reaction 1b of FIG. 1, is reacted to provide various compounds of this invention. As shown in Reaction 2d and Example 7, the 1-methyl ester may be hydrolyzed with 0.5N aqueous LiOH in tetrahydrofuran (THF) to yield the corresponding acid. Alternatively, the 1-methylester may be reduced with LiBH$_4$ in ethylether, in, accordance with Reaction 2c and as illustrated in Example 6, to yield the corresponding alcohol. This alcohol may be subsequently converted into the 5-t-butyl dimethyl siloxy derivative and reacted, in accordance with Reaction 2e, with 2,6-di-t-butyl pyridine in CH$_2$Cl$_2$ and subsequently reacted with methyl triflate (MeOTF) to form the 1-methoxy derivative. To provide other 1-hydrocarbyloxy esters the alternate Reaction 2e may be utilized whereby the 1-alcohol may be reacted with the hydrocarbyl chloride, R$_7$Cl, wherein R$_7$ is a hydrocarbyl radical comprising up to 20 carbon atoms, e.g. a C1 to C4 alkyl chloride, in the presence 4-dimethylaminopyridine (DMAP) in triethylamine and CH$_2$ Cl$_2$. Finally, the 1-methylester may be reacted, in accordance with Reaction 2a and as illustrated in Example 4, with an amine, R$_5$R$_6$NH, wherein R$_5$ and R$_6$ are selected from the group consisting of hydrogen and hydrocarbyl radicals, preferably hydrogen and C$_1$ to C$_4$ alkyl radicals, in CH$_3$OH, for example at a temperature of 55° C., to yield the corresponding amides. Such amides may be subsequently reduced with LiAlH$_4$ in THF, in accordance with Reaction 2b and as illustrated by Example 5, to yield the corresponding amines.

Figure 3:
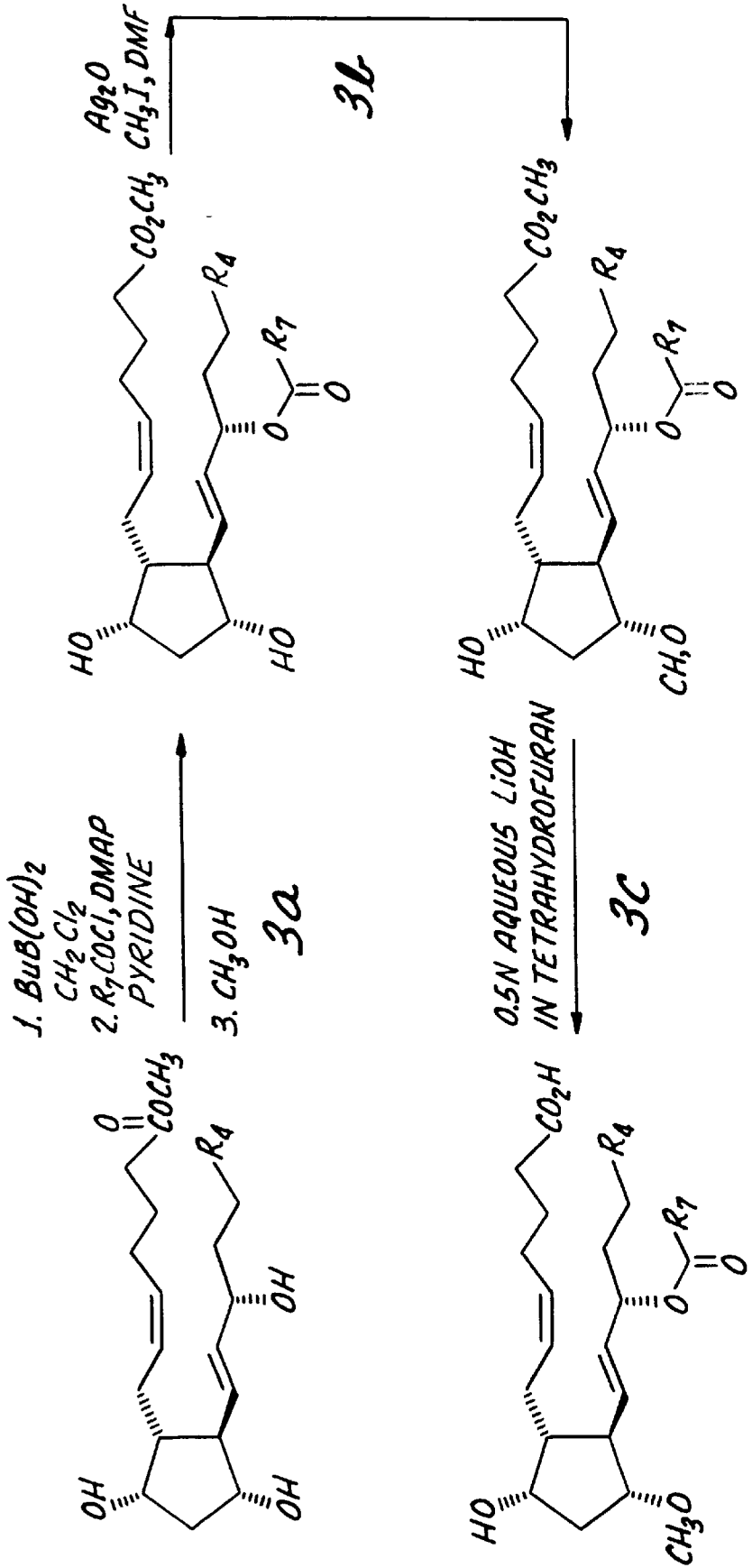
FIG. 3 is a schematic representation of the synthesis of 15-acyl analogues of certain of the ethers of the invention.

In FIG. 3 the 1-methyl ester, prepared according to the reaction scheme of FIG. 1, is reacted in accordance with Reaction 3a of FIG. 3 and as illustrated by Example 17 to yield the 15-pivaloyl ester of said 1-methyl ester. The compound is subsequently reacted in accordance with Reaction 3b of FIG. 3 and as illustrated by Example 17a to yield the 11-methoxy derivative. This compound may then be converted to the 1-acid in accordance with Reaction 3c, as illustrated by Example 17b, to yield the 11-methoxy, 15 pivaloyloxy acid of the invention.

Figure 4:
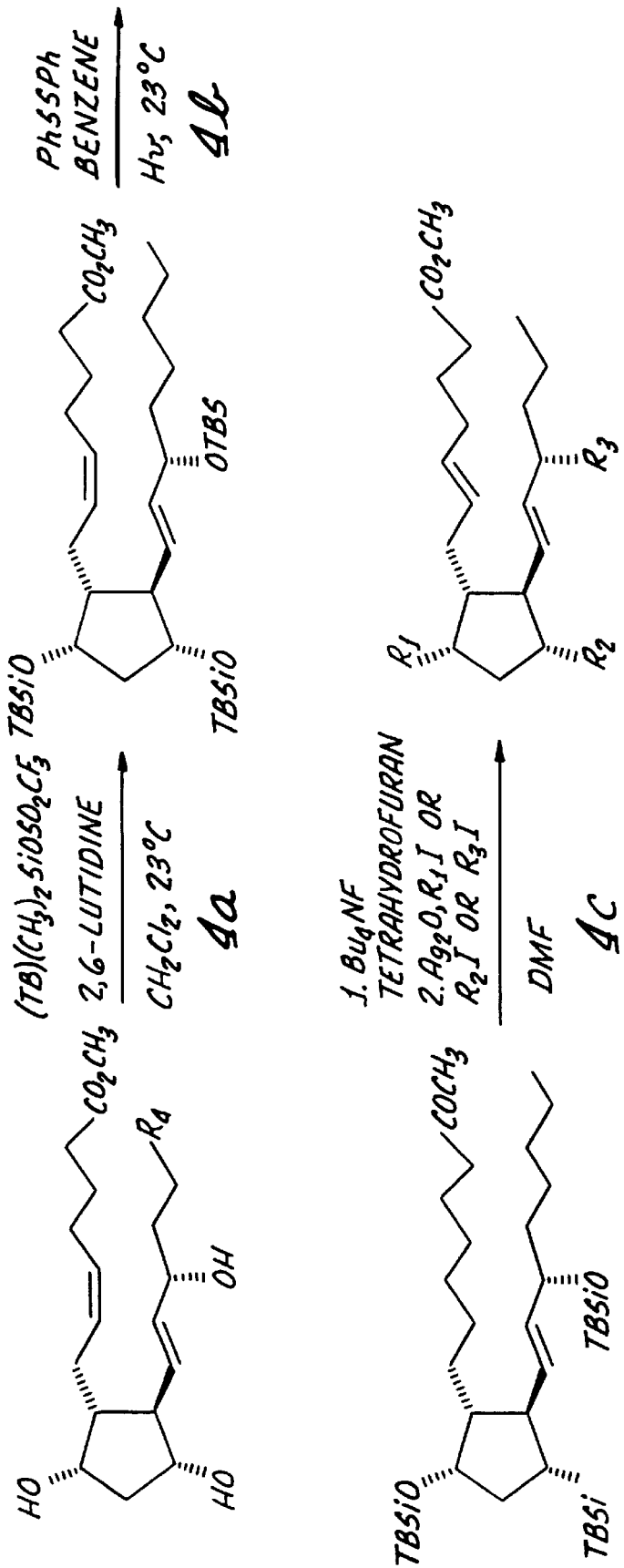
FIG. 4 is a schematic representation of the synthesis of certain of the 5, 6 trans compounds of the invention.

In FIG. 4, the 1-methylester prepared in accordance with the reaction scheme of FIG. 1, is consecutively reacted according to Reactions 1a through 1c, as illustrated in Example 18 to yield the 5-trans compounds of this invention.

The following novel compounds may be used in the pharmaceutical compositions and the methods of treatment of the present invention.

Methyl 7-[5α-Hydroxy-2β(3α-hydroxy-1E-octenyl)-3α-methoxy-cyclopentyl]-5Z-heptenoate 7-[5α-Hydroxy-2β-(3α-hydroxy-1E-octenyl)-3α-methoxy-cyclopentyl]-5Z-heptenoic acid 7-[5α-Hydroxy-2β-(3α-hydroxy-1E-octenyl)-3α-methoxy-cyclopentyl]-5Z-hepten-1-ol 7-[5α-Hydroxy-2β-(3α-pivalyl-1E-octenyl)-3α-methoxy-cyclopentyl]-5Z-heptenoic acid Methyl 7-[5α-Hydroxy-2β-(3α-pivalyl-1E-octenyl)-3α-methoxy-cyclopentyl]-5Z-heptenoate 7-[5α-Hydroxy-2β-(3α-hydroxy-1E-octenyl)-3α-methoxy-cyclopentyl]-5Z-hepten-1-pivalate Methyl 7-[5α-Hydroxy-2(3α-hydroxy-1E-octenyl)-3α-methoxy-cyclopentyl]-5E-heptenoate 7-[5α-Hydroxy-2β-(3α-hydroxy-1E-octenyl)-3α-methoxy-cyclopentyl]-5E-heptenoic acid 7-[5α-Hydroxy-2β-(3α-hydroxy-1E-octenyl)-3αmethoxy-cyclopentyl]-5E-hepten-1-ol Methyl 7-[3α-ethoxy-5α-hydroxy-2β(3α-hydroxy-1E-octenyl)-cyclopentyl)-5Z-heptenoate 7-[3α-Ethoxy-5α-hydroxy-2β-(3α-hydroxy-1E-octenyl)-cyclopentyl]-5Z-heptenoic acid 7-[3α-Ethoxy-5α-hydroxy-2β-(3α-hydroxy-1E-octenyl)-cyclopentyl]-5Z-hepten-1-ol 7-[5α-Hydroxy2β-(3α-hydroxy-1E-octenyl)-3α-methoxy-cyclopentyl]-5Z-heptenamide N,N-Dimethyl-7- [5α-hydroxy-2β-(3α-hydroxy-1E-octenyl)-3α-methoxy-cyclopentyl]-5Z-heptenamide Methyl 7-[5α-hydroxy-2β-(3α-hydroxy-1E-octenyl)-3α-(2-propenoxy)-cyclopentyl]-5Z-heptenoate 7-[5α-Hydroxy-2β-(3α-hydroxy-1E-octenyl)-3α-(2-propenoxy)-cyclopentyl]-5Z-hepten-1-ol 7-[5α-Hydroxy-2β-(3α-hydroxy-1E-octenyl)-3α-(2-propenoxy)-cyclopentyl]-5Z-heptenoic acid Methyl 7-[3α,5α-dimethoxy-2β-(3α-hydroxy-1E-octenyl)-cyclopentyl]-5Z-heptenoate 7-[3α,5α-dimethoxy-2β-(3α-hydroxy-1E-octenyl)-cyclopentyl]-5Z-heptenoic acid 7- [3α,5α-dimethoxy-2β-(3α-hydroxy-1E-octenyl)-cyclopentyl]-5Z-hepten-1-ol Methyl 7-[3α-hydroxy-2β-(3α-hydroxy-1E-octenyl)-5α-methoxy-cyclopentyl]-5Z-heptenoate 7-[3α-hydroxy-2β-(3α-hydroxy-1E-octenyl)-5α-methoxy-cyclopentyl]-5Z-heptenoic acid 7-[3α-hydroxy-2β-(3β-hydroxy-1E-octenyl)-5α-methoxy-cyclopentyl]-5Z-hepten-1-ol N-Isopropyl-7-[5α-hydroxy-2β-(3α-hydroxy-1E-octenyl)-3α-methoxy-cyclopentyl]-5Z-heptenamide N-Isopropyl-7-[5α-hydroxy-2β-(3α-hydroxy-1E-octenyl)-3α-methoxy-cyclopentyl]-5Z-heptenamine N,N-Dimethyl-7-[5α-hydroxy-2β-(3α-hydroxy-1E-octenyl)-3α-methoxy-cyclopentyl]-5Z-heptenamine 7- [5α-Hydroxy-2β-(3α-hydroxy-1E-octenyl)-3α-propoxy-cyclopentyl]-5Z-hepten-1-ol 7-[5α-Hydroxy-2β-(3αhydroxy-1E-octenyl)-3α-propoxy-cyclopentyl]-5Z-heptenoic acid Methyl-7-[5α-hydroxy-2β-(3α-hydroxy-1E-octenyl)-3αpropoxy-cyclopentyl]-5Z-heptenoate Methyl-7-[3α,5α-dihydroxy-2β-(3α-methoxy-1E-octenyl)-cyclopentyl]-5Z-heptenoate 7-[3α,5α-Dihydroxy-2β-(3α-methoxy-1E-octenyl)-cyclopentyl]-5Z-heptenoic acid 7-[3α,5α-Dihydroxy-2β-(3α-methoxy-1E-octenyl)-cyclopentyl]-5Z-hepten-1-ol 1-Acetoxy-7-3α,5α-Dihydroxy-2β-(3α-methoxy-1E-octenyl)-cyclopentyl]-5Z-heptene 7- [3α,5α-Dihydroxy-2β-(3α-methoxy-1E-octenyl)-cyclopentyl]-1-methoxy-5Z-heptene 7-[3α-ethoxy-5α-hydroxy-2β-(3α-hydroxy-1E-octenyl)-cyclopentyl]-5Z-heptenamide N-Isopropyl-7-[3α-ethoxy-5α-hydroxy-2β-(3α-hydroxy-1E-octenyl)-cyclopentyl]-5Z-heptenamide N-Isopropyl-7-([3α,5α-Dihydroxy-2α-(3β-methoxy-1E-octenyl)-cyclopentyl]-5Z-heptenamide Methyl-7-[3α,5α-Dihydroxy-2β-(3α-ethoxy-1E-octenyl)-cyclopentyl]-5Z-heptenoate 7- [3α,5α-Dihydroxy-2β-(3α-ethoxy-1E-octenyl)-cyclopentyl]-5Z-heptenoic acid Methyl 7-[3α-Butoxy-5α-hydroxy-2β-(3α-hydroxy-1E-octenyl)-cyclopentyl]-5Z-heptenoate 7-[3α-Butoxy-5α-hydroxy-2β-(3α-hydroxy-1E-octenyl)-cyclopentyl]-5Z-hepten-1-ol 7- [3α-Butoxy-5α-hydroxy-2β(3α-hydroxy-1E-octenyl)-cyclopentyl]-5Z-heptenoic acid N-Isopropyl-7-[5α-hydroxy-2β-(3α-hydroxy-1E-octenyl)-3α-propoxy-cyclopentyl]-5Z-heptenamide 7- [5α-hydroxy-2α-(3α-hydroxy-1E-octenyl)-3α-propoxy-cyclopentyl]-5Z-heptenamide Isopropyl-7-[5α-hydroxy-2β-(3α-hydroxy-1E-octenyl)-3α-propoxy-cyclopentyl]-5Z-heptenoate 7-[3α,5α-Dihydroxy-2β-(3α-methoxy-1E-octenyl)-cyclopentyl]-5Z-heptenamide Isopropyl-7-[3α,5α-dihydroxy-2β-(3α-methoxy-1E-octenyl)-cyclopentyl]-5Z-heptenoate Methyl-7-[3α,5α-Dihydroxy-2β-(3α-methoxy-5phenyl-1E-pentenyl)-cyclopentyl]-5Z-heptenoate 7- [3α,5α-Dihydroxy-2β-(3α-methoxy-5-phenyl-1E-pentenyl)-cyclopentyl]-5Z-heptenoic acid 7- [3α,5α-Dihydroxy-2β-(3α-methoxy-5-phenyl-1E-pentenyl)-cyclopentyl]-5Z-heptenamide A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium, metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 ml.

The invention is further illustrated by the following non-limiting Examples.

EXAMPLE 1
Methyl 7-[5α-Hydroxy-2β-(3αhydroxy-1E-octenyl)-3α-methoxy-cyclopentyl]-5Z-heptenoate.

In accordance with Reaction 1b of Scheme 1, 300 mg. (0.815 mmols) of the 1-methylester of $PGF_{2\alpha}$ were dissolved in 1.0 mL of dimethylformamide (DMF). To this solution was added 150.5 mg. (0.649 mmol) of $Ag_2O$ and 173.6 mg. (1.22 mmol) of methyliodide (MeI) and the resulting solution was stirred at 23° C. to obtain (8% yield) of the named compound in admixture with the 9-mono (4% yield), 15-mono and 11, 15 bis (14% yield) methyl ethers of the 1-methylester of $PGF_{2\alpha}$. (The compounds obtained in admixture with the named compound may also be referred to as the 5α-methoxy, 2β-(3α-methoxy-1E-octenyl) and 2β-(3α-methoxy-1E-octenyl)-3αmethoxy analogues of the named compound, respectively. The ethers were separated using high pressure liquid chromatography (HPLC) and eluting the admixture with a 1 to 1 mixture of hexane (hex) and ethylacetate (EtOAc) over a Whatman PARTISIL 10 PAK column.

EXAMPLE 1a
Methyl-7-[5α-hydroxy-2β-(3α-hydroxy-1E-octenyl)-3αpropoxycyclopentyl]-5Z-heptenoate.

The named compound may be prepared by substitution of n-propyliodide for methyl iodide in the procedure of Example 1.

EXAMPLE 1b
Methyl-7-[3α-ethoxy-5α-hydroxy-2β-(3α-hydroxy-1E-octenyl)-cyclopentyl]-5Z-heptenoate.

The named compound may be prepared by substitution of ethyliodide for methyl iodide in the procedure of Example 1.

EXAMPLE 1c
Methyl-7-[3α-Butoxy-5α-hydroxy-2β-(3α-hydroxy-1E-octenyl]-cyclopentyl]-5Z-heptenoate.

The named compound may be prepared by substitution of n-butyliodide for methyl iodide in the procedure of Example 1.

EXAMPLE 1d
Methyl-7-[5α-hydroxy-2β-(3α-hydroxy-1E-octenyl)-3α(2-propenoxy)-cyclopentyl]-5Z-heptenoate.

The procedure of Example 1 is repeated using allyliodide in place of methyliodide to yield the named compound.

EXAMPLE 2
Isopropyl 7-[5α-Hydroxy-2β(3α-hydroxy-1E-octenyl)-3α-methoxy-cyclopentyl]-5Z-heptenoate The procedure of Example 1 was repeated except that the 1-isopropylester of $PGF_{2\alpha}$ was utilized as the reactant in place of the corresponding methyl ester to yield a reaction solution containing an admixture of mono and bis methyl ethers. The reaction solution was diluted with $CH_2Cl_2$ and filtered through Celite. The filtrate was concentrated under vacuum, diluted with ethylether ($Et_2O$) and washed twice with water. The organic layer was dried over anhydrous $MgSO_4$, filtered and concentrated under vacuum. The residue was purified by flash column chromatography (FCC) with an eluant of 1 to 1 hex/EtOAc to yield 120 mg. (59% yield) of the named compound and the 15-methyl ether analogue, thereof. 80% of the purified mixture was the named compound.

EXAMPLE 3
Isopropyl 7-[5α-Hydroxy-2β-(3α-hydroxy-1E-octenyl)-3α-propoxy-cyclopentyl]-5Z-heptenoate 20 mg. (0.050 mmol) of $PGF_{2\alpha}$ was combined with 47 mg (0.252 mmol of O-isopropyl N, N'-diisopropyl isourea in 1.0 mL of benzene and heated at 85° C. for 20 hours. The reaction mixture was concentrated in vacuo and the residue was purified by FCC using a 3 to 1 mixture of hexane and EtOAc to yield 16.3 mg. (74% yield) of the 11-isopropylester of $PGF_{2\alpha}$. The named compound may be prepared from said 11-isopropyl ester by substitution of propyliodide for methyliodide in the procedure of Example 2.

EXAMPLE 4
N-Isopropyl-7-(5α-hydroxy-2β-(3αhydroxy-1E-octenyl)-3αmethoxy-cyclopentyl]-5Z-heptenamide In accordance with Reaction 2a of FIG. 2, 220 mg. (0.5759 mmol) of the compound of Example 1 were mixed with 549 mg (5.759 mmol) of isopropylamine hydrochloride in 6.0 mL of isopropylamine and heated in a sealed tube for 72 hours at 75° C. The reaction mixture was cooled to room temperature, diluted with EtOAc and washed with water. The organic layer was treated as in Example 2 to yield 23.5 mg (10% yield) of the named compound.

EXAMPLE 4a
N,N-Dimethyl-7-(5α-hydroxy-2β-(3α-hydroxy-1E-octenyl)-3α-methoxy-cyclopentyl]-5Z-heptenamide The named compound is prepared in accordance with the procedure of Example 4 by using methylamine hydrochloride in methylamine.

EXAMPLE 4b
N-Isopropyl-7-(3αethoxy-5α-hydroxy-2β-(3α-hydroxy-1E-octenyl)-cyclopentyl]-5Z-heptenamide The named compound is prepared by substituting the compound of Example 1b in the process of Example 4.

EXAMPLE 4c
N-Isopropyl-7-(5α-hydroxy-2β-(3α-hydroxy-1E-octenyl)-3α-propoxy-cyclopentyl]-5Z-heptenamide The named compound is prepared by substituting the compound of Example 1a in the process of Example 4.

EXAMPLE 4d
N,N-Dimethyl-7-(5α-hydroxy-2β-(3α-hydroxy-1E-octenyl)-3α-methoxy-cyclopentyl]-5Z-heptenamide Dimethylamine (~5 ml) was condensed in a tube containing 100 mg (0.1639 mmol) of the 5-t-butyldimethylsiloxy, 3-methoxy derivative of $PGF_{2\alpha}$, methylester dissolved in 6.0 mL of $CH_3OH$. The resultant solution was stirred in a sealed glass tube for 48 hours and concentrated in vacuo. The residue diluted with THY (1.0 mL) and treated with $Bu_4NF$ (0.26 mL of a 1.0M solution, 0.262 mmol) at 23° C. After 16 hours, the reaction was diluted with $Et_2O$ and washedwith $H_2O$. The organic portion was dried ($MgSO_4$), filtered and concentrated in vacuo. FCC (100% EtOAc followed by 9:1 $CH_2Cl_2$/MeOH) gave 24.2 mg. (39%) of the product.

EXAMPLE 5
N-Isopropyl-7-(5α-hydroxy-2β-(3α-hydroxy-1E-octenyl)-3α-methoxy-cyclopentyl]-5Z-heptenamine In accordance with Reaction 2b of FIG. 2, 75. mg of the compound of Example 4, dissolved in 2.0 mL of tetrahydrofuran (THF) were treated with 34.6 mg. (0.9165. mmol) of lithium aluminumhydride (LAH) at 23° C. After 24 hours, the reaction mixture was quenched with 2.0 N NaOH and extracted with EtOAc. The organic layer was dried over anhydrous MgSO4, filtered and concentrated under vacuum. The residue was purified with FCC using a 6:1:0.1 mixture of $CH_2Cl_2$/MeOH/NH4OH to yield 19.0 mg. (26% yield) of the named compound.

EXAMPLE 5a
N,N-Dimethyl-7-(5α-hydroxy-2β-(3α-hydroxy-1E-octenyl)-3α-methoxy-cyclopentyl]-5Z-heptenamine The named compound is prepared by substitution of the compound of Example 4a in the procedure of example 5.

EXAMPLE 6
7-(5α-Hydroxy2β-(3α-hydroxy-1E-octenyl)-3α-methoxy-cyclopentyl]-5Z-hepten-1-ol In accordance with Reaction 2c of FIG. 2, 20.2 mg (0.052 mmol) of the compound of Example 1 were dissolved in 1.5 mL of $Et_2O$ and treated with 2.3 mg (0.105 mmol) of $LiBH_4$ to yield a reaction mixture comprising the named product. The resulting product was purified by FCC with a 1 to 1 mixture of hex/EtOAc followed by 100% EtOAc to yield 16.3 mg. (87%) of the named compound.

EXAMPLE 6a
7-[3α-Ethoxy-5α-hydroxy-2β-(3α-hydroxy-1E-octenyl)-cyclopentyl]-5Z-hepten-1-ol The named compound is prepared by substituting the compound of Example 1b in the process of Example 6.

EXAMPLE 6b
7-[3α-Butoxy-5α-hydroxy-2β-(3α-hydroxy-1E-octenyl)-cyclopentyl]-5Z-hepten-1-ol The named compound is prepared by substituting the compound of Example 1c in the process of Example 6.

EXAMPLE 6c
7-[3αPropoxy-5α-hydroxy-2β-(3α-hydroxy-1E-octenyl)-cyclopentyl]-5Z-hepten-1-ol The named compound is prepared by substituting the compound of Example 1(a) in the process of Example 6.

EXAMPLE 6d
7-[5α-Hydroxy-2β-(3α-hydroxy-1E-octenyl)-3α-(2-propenoxy)-cyclopentyl]-5Z-hepten-1-ol The procedure of Example 6 is repeated using the compound of Example 1(d) as the starting material to yield the named compound.

EXAMPLE 7
7-[5α-Hydroxy-2β-(3α-hydroxy-1E-octenyl)-3α-methoxy-cyclopentyl]-5Z-heptenoic acid 40 mg (0.1047 mmol) of the compound of Example 1 were dissolved in a mixture of 0.31 mL of 0.5N aqueous LiOH and 0.62 mL of THF in accordance with Reaction 2d of Scheme 2. After the reaction mixture was acidified with 10% aqueous citric acid and extracted with $CH_2Cl_2$. The organic portion was dried ($Na_2SO_4$), filtered and concentrated in vacuo. The residue was purified by FCC using a 95 to 5 mixture of EtOAc and MeOH to yield 28.6 mg. (75% yield) of the named compound.

EXAMPLE 7a
7-[5α-Hydroxy-2β-(3α-hydroxy-1E-octenyl)-3α-propoxy-cyclopentyl]-5Z-heptenoic acid The named compound is prepared by substituting the compound of Example 1a in the procedure of Example 7.

EXAMPLE 7b
7-[3α-Ethoxy-5α-hydroxy-2β-(3α-hydroxy-1E-octenyl)-cyclopentyl]-5Z-heptenoic acid The named compound is prepared by substituting the compound of Example 1b in the procedure of Example 7.

EXAMPLE 7c
7-[3α-Butoxy-5α-hydroxy-2β-(3α-hydroxy-1E-octenyl)-cyclopentyl]-5Z-heptenoic acid The named compound is prepared by substituting the compound of Example 1c in the procedure of Example 7.

EXAMPLE 7d
7-[5α-Hydroxy-2β-(3α-hydroxy-1E-octenyl)-3α-(2-propenoxy)-cyclopentyl]-5Z-heptenoic acid The named compound is prepared by substituting the compound of Example 1d in the procedure of Example 7.

EXAMPLE 8
7-[5α-Hydroxy-2β-(3α-hydroxy-1E-octenyl)-3α-methoxy-cyclopentyl]-5Z-heptenamide According to the procedures described for Example 4, the compound of Example 1 is reacted with $NH_4Cl$ dissolved in $NH_3$ to yield the named compound.

EXAMPLE 8a
7-[3α-Ethoxy-5α-Hydroxy-2β-(3α-hydroxy-1E-octenyl)-cyclopentyl]-5Z-heptenamide In accordance with Example 8, 100 mg (0.252 mmol) of the compound of Example 1(b) is reacted with 135 mg (2.52 mmol) of $NH_4Cl$ dissolved in 5 mL of $NH_3$ to give the named compound in 69% yield.

EXAMPLE 8b
7-[5α-Hydroxy-2β-(3α-hydroxy-1E-octenyl)-3αpropoxy-cyclopentyl]-5Z-heptenamide In accordance with Example 8, 52 mg (0.127 mmol) of the compound of Example 1(a) is reacted with 68 mg (1.27 mmol) of $NH_4Cl$ dissolved in 4.5 mL of $NH_3$ to give the named compound in 86% yield.

EXAMPLE 9
7-[5α-Hydroxy-2β-(3α-hydroxy-1E-octenyl)-3α-methoxy-cyclopentyl]-1-pivaloyloxy 5Z-heptene The 1-t-butyldimethylsilyl ester of 3-methoxy $PGF_{2\alpha}$ and 5.2 mg (0.239 mmol) of $LiBH_4$ was dissolved in 1.0 mL of ethylether and stirred for 16 hours at 23° C. The reaction mixture was quenched with 2.0 N aqueous NaOH and extracted with $CH_2Cl_2$. The organic portion was dried over anhydrous $Na_2SO_4$, filtered and concentrated under vacuum. The residue was dissolved in 0.5 mL of pyridine and cooled to 0° C. 17.7 uL(0.143 mmol) of trimethylacetyl chloride were added and after 24 hours the reaction was diluted with EtOAc, washed with saturated aqueous $NH_4Cl$ and brine and dried over anhydrous $MgSO_4$. The dried product was filtered and concentrated under vacuum before purifying by use of FCC and a 1 to 1 mixture of hexane and EtOAc to yield 15.9 mg (31% yield of the named compound).

EXAMPLE 10

7-[3α,5α-Dihydroxy-2β-(3α-methoxy-1E-octenyl)-cyclopentyl]-1-methoxy-5Z-heptene

In accordance with Reaction 2e of Scheme 2, a solution of the compound of Example 6 and 0.46 mL 2, 6-di-t-butylpyridine (2.058 mmol) in 2.0 mL $CH_2Cl_2$ was treated with methyl triflate (194 ul, 1.715 mmol) and stirred for 48 hours at 23° C. The reaction mixture was quenched with saturated aqueous $NaHCO_3$ and extracted with $CH_2Cl_2$. The combined organic portion was dried over anhydrous $Na_2SO_4$, filtered and concentrated in vacuo. The residue was diluted with 2.0 mL of THF and 1.4 mL of a 1.0M solution of $Bu_4NF$ in THT. After 16 hours, the reaction was diluted with EtOAc and washed with $H_2O$. The organic portion was dried over anhydrous $MgSO_4$, filtered and concentrated in vacuo. Treating by FCC with 1:1 hex/EtOAc gave 66.1 mg (53% yield) of the named compound.

EXAMPLE 11

1-Acetoxy-7-[3α,5α-Dihydroxy-2β-(3α-methoxy-1E-octenyl)-cyclopentyl]-5Z-heptene

1-Acetoxy-7-[3α,5α-t-butyldimethylsiloxy-2β-(3α-meth-oxy-1E-octenyl)-cyclopentyl]-5Z-heptene is reacted with $Bu_4NF$ in THF at room temperature to yield the named compound.

EXAMPLE 12

Methyl 7-[3α-Hydroxy-2β-(3α-hydroxy-1E-octenyl)-5α-methoxy-cyclopentyl]-5Z-heptenoate The named compound is prepared in accordance with the procedure of Example 1.

EXAMPLE 12a

7-[3α-Hydroxy-2β(3α-hydroxy-1E-octenyl)-5α-methoxy-cyclopentyl]-5Z-heptenoic acid The named compound is prepared by reacting the compound of Example 12 in accordance with the process of Example 7.

EXAMPLE 12b

7-[3α-Hydroxy-2β-(3α-hydroxy-1E-octenyl)-5α-methoxy-cyclopentyl]-5Z-hepten-1-ol

The named compound is prepared by reacting the 1-t-butyl dimethylsiloxy ester of the compound of Example 12(a) in accordance with the process of Example 6.

EXAMPLE 13

7-[3α-5α-Dihydroxy-2β-(3α-methoxy-1E-octenyl)-cyclopentyl]-5Z hepten-1-ol

The 15-monomethyl ether of Example 1 is reacted in accordance with the process of Example 6 to yield the named compound.

EXAMPLE 13a

7-[3α-5α-Dihydroxy-2β-(3α-methoxy-1E-octenyl)-cyclopentyl]-5Z-heptenoic acid

The 15-monomethyl ester of Example 1 is reacted in accordance with the process of Example 7 to yield the named compound.

EXAMPLE 13b

Isopropyl-7-[3α-5α-Dihydroxy-2β-(3α-methoxy-1E-octenyl)-cyclopentyl]-5Z-heptenamide The 15-monomethyl ester of Example 1 is reacted in accordance with the process of Example 4 to yield the named compound.

EXAMPLE 13c

7-[3α-5α-Dihydroxy-2β-(3α-methoxy-1E-octenyl)-cyclopentyl]-5Z-heptenamide

The 15-monomethyl ester of Example 1 is reacted in accordance with the process of Example 8 to yield the named compound.

EXAMPLE 14

Methyl-7-[3α-5α-Dihydroxy-2β(3α-ethoxy-1E-octenyl)-cyclopentyl]-5Z-heptenoate

The named compound is prepared in accordance with the process of Example 1 by replacing methyliodide with ethyl iodide.

EXAMPLE 14a

7-[3α-5α-Dihydroxy-2β-(3αethoxy-1E-octenyl)-cyclopentyl]-5Z-heptenoic acid

The named compound is prepared by reacting the compound of Example 14 in accordance with the process of Example 7.

EXAMPLE 14b

N-Isopropyl-7-[3α-5α-Dihydroxy-2β-(3α-ethoxy-1E-octenyl)-cyclopentyl]-5Z-heptenamide The named compound is prepared by reacting the compound of Example 14 in accordance with the process of Example 4.

EXAMPLE 14c

7-[3α-5α-Dihydroxy-2β-(3α-ethoxy-1E-octenyl)-cyclopentyl]-5Z-heptenamide

The named compound is prepared by reacting the compound of Example 14 in accordance with the process of Example 8.

EXAMPLE 15

Methyl-7-[3α-5α-Dimethoxy-2β-(3α-hydroxy-1E-octenyl) cyclopentyl]-5Z-heptenoate

The named compound is isolated from the reaction product of Example 1.

EXAMPLE 15a

7-[3α-5α-Dimethoxy-2β-(3α-hydroxy-1E-octenyl)-cyclopentyl]-5Z-heptenoic acid

The named compound is prepared by substituting the 3, 5-dimethylether of Example 15 in the process of Example 7.

EXAMPLE 15b

7-[3α-5α-Dimethoxy-2β-(3α-hydroxy-1E-octenyl)-cyclopentyl]-5Z-hepten-1-ol

The named compound is prepared by substituting the 3, 5-dimethylether of Example 15 in the process of Example 6.

EXAMPLE 16

Methyl-7-[3α-5α-Dihydroxy-2β-(3α-methoxy-5phenyl-1E-pentenyl)-cyclopentyl]-5Z-heptenoate The named compound is prepared according to the process described in Example 1 by substituting the 1-methylester of 17-phenyl, 18, 19, 20trinor $PGF_{2\alpha}$, for the 1-methylester of $PGF_{2\alpha}$.

EXAMPLE 16a
7-[3α-5α-Dihydroxy-2β-(3α-methoxy-5-phenyl-1E-pentenyl)-cyclopentyl]-5Z-heptenoic acid The named compound is prepared by substituting the compound of Example 16 in the process of Example 7.

EXAMPLE 16 b
7-[3α-5α-Dihydroxy-2β-2β(3α-methoxy-5-phenyl-1E-pentenyl)-cyclopentyl]-5Z-heptenamide The named compound is prepared by substituting the compound of Example 16 in the process of Example 8.

EXAMPLE 17
Methyl 7-[3α, 5αDihydroxy-2β(3α-pivalyl-1E-octenyl)-cyclopentyl]-5Z-heptenoate $PGF_{2\alpha}$ (40.4 mg 0.114 mmol) was suspended in$Et_2O$(1 mL) and cooled to 0°. A solution of $CH_2N_2$ in $Et_2O$ was added dropwise to the above suspension until a yellow color persisted. The solution was warmed to 25° for 30 minutes before concentration to yield the $PGF_{2\alpha}$ methyl ester as an oil. The crude ester was combined with 14 mg., (0.137 mmol) n-butyl boronic acid $(BuB(OH)_2)$ in 0.25 mL of $CH_2Cl_2$ and heated at reflux temperature for 30 minutes. The reaction mixture was concentrated and the residue dissolved in dry benzene. The benzene was evaporated under reduced pressure. The process was repeated twice to remove traces of water present from the reaction, leading to boronate ester, which was subsequently dissolved in 0.2 mL of dry pyridine and treated with pivalyl chloride (0.043 mL, 0.34 mmol) and 4-DMAP (about 1 mg). The reaction mixture was stirred at 25° for 14 h before being concentrated. The residue was dissolved in EtOAc(10 mL) and washed with 10% citric acid (7 mL). The aqueous phase was extracted with EtOAc and the combined organic extracts were washed with brine, dried over anhydrous $MgSO_4$, filtered and concentrated. The residue was dissolved in MeOH (3 mL) and stirred at 25° for 2 h. The solvent was removed and replaced with fresh MeOH. This process was repeated once more. After removal of solvent, the residue was purified by chromatography (silica, 50–60% EtOAc/hexane) to yield the named product as an oil.

EXAMPLE 17a
Methyl-7-[5α-Hydroxy-2β-(3α-pivalyl-1E-octenyl)-3α-methoxy-cyclopentyl]-5Z-heptenoate The named compound is prepared by substituting compound of Example 17 for the 1-methylester of $PGF_{2\alpha}$ in the process of Example 1. (See Reaction 3b of FIG. 3.)

EXAMPLE 17b
7-[5α-Hydroxy-2β-(3α-pivalyl-1E-octenyl)-3α-methoxy-cyclopentyl]-5Z-heptenoic acid The named compound is prepared by substituting the compound of Example 17a in the process of Example 7. (See Reaction 3c of FIG. 3.)

EXAMPLE 18
Methyl-7-[5α-Hydroxy-2β-(3α-hydroxy-1E-octenyl)-3α-methoxy-cyclopentyl]-5E-heptenoate 987 mg (2.68 mmol) of the 1-methyl ester of $PGF_{2\alpha}$ was mixed with 1.43 g (13.41 mmol) of 2, 6-lutidine and 2.48 g (9.38 mmol) of t-butyldimethylsiloxytriflate $[(TB)(CH_3)SiOSO_2CF_3]$ in 13.4 mL of $CH_2Cl_2$ and the solution was stirred for 16 h to yield the tri-(t-butyldimethylsiloxy) ester of the 1-methyl ester of $PGF_{2\alpha}$. (See Reaction 4a of FIG. 4.) The triester was purified by elution (using FCC techniques) with a 30 to 1 solution of hexane and EtOAc 312 mg (0.439 mmols) of the resulting triester was combined with 2.7 mg (0.0088 mmol) of diphenylsulfide in 4.4 mL of benzene and the resulting solution was stirred under long wave UV light exposure for 12 hours. (See Reaction 4b of FIG. 4.) The resulting solution was concentrated under vacuum and purified by elution, as above, with a 20 to 2 solution of hexane and EtOAc to yield 296.1 mg (95% yield) of the 5-trans triester. 318 mg (0.447 mmol) of the 5-trans triester were combined with 2.7 mL of a 1.0M solution of $Bu_4NF$ in THF and 4.4 mL of 1. The solution was stirred overnight at 23° C., diluted with EtOAc, washed with $H_2O$ and brine and the organic portion was 5.5 filtered, concentrated under vacuum and purified, using FCC techniques and 100% EtOAc. to yield 123.3 mg (75% yield) of the triol of the 5-trans 1-methyl ester of PGF2α.

The triol was substituted in the process of Example 1 to yield the named compound. (See Reaction 4c of FIG. 4.)

EXAMPLE 18a
7-[5α-Hydroxy-2β-(3α-Hydroxy-1E-octenyl)-3α-methoxy-cyclopentyl]-5E-heptenoic acid The named compound is prepared by substituting the compound of Example 18 in the process of Example 7.

EXAMPLE 18b
7-[5α-Hydroxy-2β-(3α-Hydroxy-1E-octenyl)-3α-methoxy-cyclopentyl]-5E-hepten-1-ol The named compound is prepared by substituting the compound of Example 18 in the process of Example 6.

EXAMPLE 19
Methyl-7-[3α-methoxy-5α-hydroxy-2β-(3β-methoxy-1E-octenyl)-cyclopentyl]-5Z-heptenoate The named compound is isolated from the reaction product of Example 1.

EXAMPLE 19a
7-[3α-methoxy-5α-hydroxy-2β-(3α-methoxy-1E-octenyl)-cyclopentyl]-5Z-heptenoic acid The named compound is prepared by substituting the dimethylether of Example 19 in the process of Example 7.

EXAMPLE 19b
7-[3α-methoxy-5α-hydroxy-2β-(3α-methoxy-1E-octenyl)-cyclopentyl]-5Z-hepten-1-ol The named compound is prepared by substituting the dimethylether of Example 19 in the process of Example 6.

EXAMPLE 20
Effects of Intraocular Pressure

The effects of certain of the above examples on intraocular pressure are provided in the following Table 1. The compounds were prepared at the said concentrations in a vehicle comprising 0.1% polysorbate 80 and 10 mM TRIS base. Dogs were treated by administering 25 ul to the ocular surface, the contralateral eye received vehicle as a control. Intraocular pressure was measured by application pneumatonometry. Dog intraocular pressure was measured immediately before drug administration and at 4 hours thereafter.

The examples which show excellent IOP-lowering effect include Examples 1, 1a, 1b; 6. and 6a wherein the 11 position is substituted with a lower alkyl ether, i.e. a $C_1$ to $C_3$ alkyl ether and the 1-position is a lower alkyl ester, e.g. a methyl ester, or an alcohol group. Furthermore, a comparison of Example 1 and 18 shows that the 5-trans or 5-cis isomers are substantially similar in their IOP-lowering effect. Finally, the 9 and 15-substituted lower alkyl ether derivatives wherein the 1-position is substituted with a lower alkyl ester group are also very effective in lowering IOP. (Compare Examples 12 and the 15-monoester of Example 1)

In contrast, various derivatives wherein the 11-position is substituted with a lower alkyl ether group and the 1-position is an add or an amino group showing lower effect in lowering IOP at a concentration of 0.1%. (See Examples 4a, 4b, 4c, 5, 7d, 18a, 19a and 19b.) However, it is believed that higher concentrations would have greater effect in lowering IOP.

In Table 1, hyperemia is measured by visual estimation. Slight hyperemia would be given a value between 0 and 0.5; moderate hyperemia would be given a value from 0.5 to 1.0 and severe hyperemia would be given a value of greater than 1.0. Miosis would be evaluated as 0 (nothing), slight (slite) or pinpoint (pin), i.e., the pupil would be the size of a pinpoint.

TABLE 1

| EXAMPLE | DOG IOP | HYPEREMIA/ MIOSIS |
|---|---|---|
| 1 | 0.01/+3.0 | 0.03/0 |
|  | 0.1%/−6.2 | 0.50/pin |
| 6 | 0.01/−1.6 | 0.08/0 |
|  | 0.1%/−5.7 | 0.75/pin |
| 17a | 0.1%/−1.3 | 0.03/slite |
| 17 | 0.1%/−2.5 | 0.82/pin |
| 9 | 0.1%/−2.5 | 0.17/slite |
| 18 | 0.01/0 | 0.08/slite |
|  | 0.1%/−6.3 | 0.03/slite |
| 18a | 0.1%/0.0 | 0/0 |
| 18b | 0.1%/−3.0 | 0.03/slite |
| 1b | 0.1%/−5.2 | 0.44/pin |
| 7b | 0.1%/−3.9 | 0.75/pin |
| 6a | 0.1%/−6.5 | 0.03/pin |
|  | 0.1%/0.0 |  |
| 8 | 0.1%/−3.3 | 0.56/pin |
| 4a | 0.1%/0.0 | 0.33/slite |
| 1d | 0.1%/−3.8 | 0.66/pin |
| 6d | 0.1%/−2.3 | 0.58/pin |
| 7d | 0.1%/0.0 | 0.31/pin |
| 19 | 0.1%/−2.4 | 0.75/pin |
| 19a | 0.1%/0.0 | 0.04/0 |
| 19b | 0.1%/0.0 | 0/slite |
| 12 | 0.01/−3.3 | 0/slite |
|  | 0.1%/−7.8 | 0.53/pin |
| 12a | 0.1%/−2.8 | 0.25/slite |
| 12b | 0.1%/−4.2 | 0/slite |
| 5 | 0.1%/0.0 | 0.08/0 |
| 6c | 0.1%/−2.0 | 0.29/slite |
| 7a | 0.1%/−3.9 | 0.54/pin |
|  | 0.01/0 | 0.62/slite |
| 1a | 0.1%/−7.6 | 0.83/pin |
|  | 0.01/0 | 0.29/slite |
| 1 | 0.1%/7.8 | 0.89/pin |
| (15-mono ester) | 0.01/−2.0 | 0.83/pin |
|  | 0.1%/−4.5 | 1.34/pin |
| 11 | 0.1%/−2.9 | 0.42/slite |
| 10 | 0.1%/−1.8 | 0/0 |
| 8a | 0.1%/0 | 0.29/pin |
|  | 0.1%/−2.9 | 0.21/pin |
| 4b | 0.1%/0 | 0.08/slite |
| 13b | 0.0.1%/−3.9 | 0.5/pin |
| 14 | 0.1%/−4.5 | 0.50/pin |
| 1c | 0.1%/−4.4 | 1.17/pin |
| 6b |  |  |
| 7c | 0.1%/−1.6 | 0.70/0 |
| 4c | 0.1%/0 | 0/0 |
| 8b | 0.1%/−3.8 | 0.79/pin |
| 2a | 0.1%/−1.8 | 0.47/pin |
| 13c | 0.1%/−3.2 | 0.59/pin |
|  | 0.01%/−4.0 | 0.44/pin |
| 14d | 0.1%/−2.7 | 0.46/pin |
|  | 0.1%/−5.1 | 0.81/pin |
| 2 | 0.1%/−4.2 | 0.56/pin |
| 16a | 0.1%/−3.8 | ND/pin |
| 16b | 0.1%/−4.4 | 0.47/pin |

The foregoing description details specific methods and compositions that can be employed to practice the present invention, and represents the best mode contemplated.

However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

I claim:

1. A method of treating cardiovascular, pulmonary-respiratory gastrointestinal, reproductive, allergic disease, shock and glaucoma which comprises applying to the eye an amount sufficient to treat ocular hypertension of a compound of formula (I)

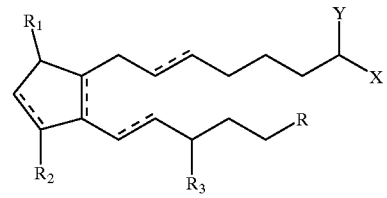

wherein either the cyclopentane(ene) radical or the α or ω chain may be unsaturated; R is a hydrocarbyl radical or a heteroatom substituted hydrocarbyl radical comprising up to ten carbon atoms and one or more of the hydrogen or carbon radicals in said hydrocarbyl radical may be substituted with oxygen, sulfur, nitrogen, phosphorus or halogen; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical.

2. The method of claim 1 wherein in said compound of formula (I) one of $R_1$, $R_2$, or $R_3$ is alkyloxy and the others are hydroxy radicals.

3. The method of claim 1 wherein said compound is the formula (II)

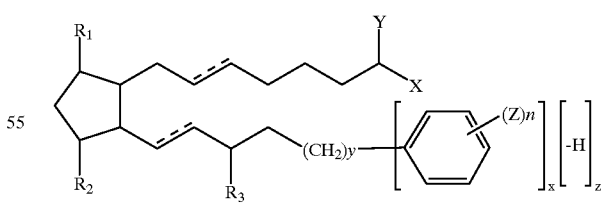

wherein y is 0 or an integer of from 1 to 5, Z is a radical selected from the group consisting of halo, nitro, amino, thiol, hydroxy, alkyloxy and alkylcarboxy; n is 0 or an integer of from 1 to 3; x is 0 or 1 and z is 0 or 1, wherein x is 0, when z is 1 and x is 1, when z is 0.

4. The method of claim 3 wherein said compound is a compound of the formula (III)

5. The method of claim 3 wherein said compound is a compound of the formula IV.

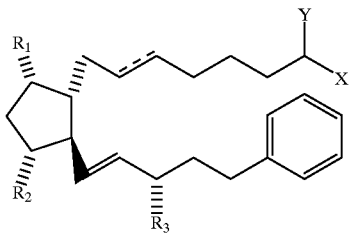

III

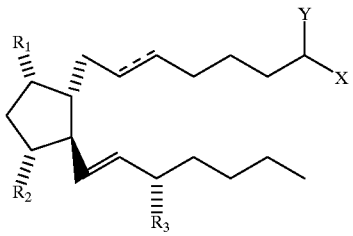

IV

6. A method of treating ocular hypertension which comprises applying to the eye an amount sufficient to treat ocular hypertension of a compound of formula (I)

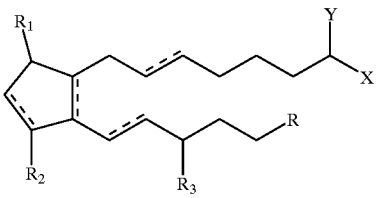

wherein either the cyclopentane(ene) radical or the α or ω chain may be unsaturated; R is pyridyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo radical, X is not an amino or a mono or diakyl amino radical.

7. The method of claim 6 wherein in said compound of formula (I) one of $R_1$, $R_2$, or $R_3$ is alkyloxy and the others are hydroxy radicals.

8. A pharmaceutical composition comprising a therapeutically effective amount of a compound of formula(I)

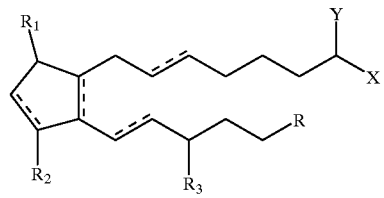

wherein either the cyclopentane(ene) radical or the α or ω chain may be unsaturated; R is pyridyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo radical X is not an amino or a mono or diakyl amino radical.

9. An ophthalmic solution comprising a therapeutically effective amount of a compound of formula (I)

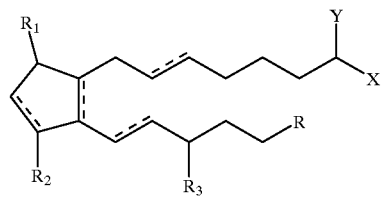

wherein either the cyclopentane(ene) radical or the α or ω chain may be unsaturated; R is pyridyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo radical X is not an amino or a mono or diakyl amino radical.

10. The ophthalmic solution of claim 9 comprising at least one ingredient selected from the group of an ophthalmically acceptable preservative, buffer system, antioxidant and chelating agent.

11. The ophthalmic solution of claim 9 wherein in said compound of formula (I) one of $R_1$, $R_2$, or $R_3$ is alkyloxy and the others are hydroxy radicals.

12. A pharmaceutical product, comprising a container adapted to dispense its contents in metered form; and an ophthalmic solution therein, as defined in claim 9.

13. A compound of the formula(I)

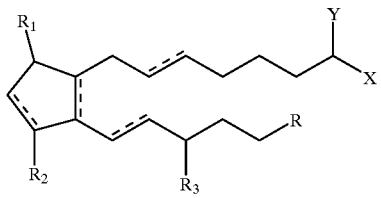

wherein either cyclopentane(ene) radical or the α or ω chain may be unsaturated; R is pyridyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo radical X is not an amino or a mono or diakyl amino radical.

14. A compound according to claim 11 wherein in said compound of formula (I) one of $R_1$, $R_2$, or $R_3$ is alkyloxy and the others are hydroxy radicals.

15. A method of treating ocular hypertension which comprises applying to the eye an amount sufficient to treat ocular hypertension of a compound of formula (I)

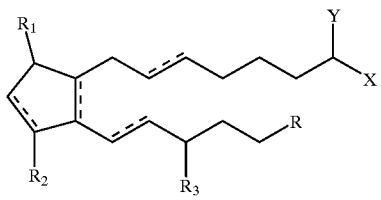

wherein either the cyclopentane(ene) radical or the α or ω chain may be unsaturated; R is furanyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo, X is not amino or a mono or diakyl amino radical.

16. The method of claim 15 wherein in said compound of formula (I) one of $R_1$, $R_2$, or $R_3$ is alkyloxy and the others are hydroxy radicals.

17. An ophthalmic solution comprising a therapeutically effective amount of a compound of formula (I)

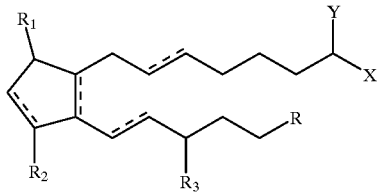

wherein either the cyclopentane(ene) radical or the α or ω chain may be unsaturated; R is furanyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo, X is not amino or a mono or diakyl amino radical.

18. A pharmaceutical composition comprising a therapeutically effective amount of a compound of formula(I)

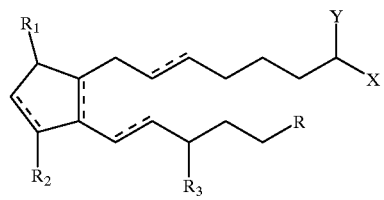

wherein either the cyclopentane(ene) radical or the α or ω chain may be unsaturated; R is furanyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo, X is not amino or a mono or dialkyl amino radical.

19. The ophthalmic solution of claim 17 comprising at least one ingredient selected from the group of an ophthalmically acceptable preservative, buffer system, antioxidant and chelating agent.

20. The ophthalmic solution of claim 17 wherein in said compound of formula (I) one of $R_1$, $R_2$, or $R_3$ is alkyloxy and the others are hydroxy radicals.

21. A compound of the formula(I)

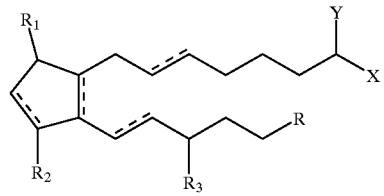

wherein either cyclopentane(ene) radical or the α or ω chain may be unsaturated; R is furanyl; $R_1$, $R_2$ and $R_3$ are selected from the group consisting of hydroxy, hydrocarbyloxy and heteroatom substituted hydrocarbyloxy wherein said hydrocarbyl radical comprises up to 20 carbon atoms; Y represents 2 hydrogen radicals or an oxo radical and X represents a hydroxyl, a hydrocarbylcarboxy, a hydrocarbyloxy, an amino or a mono or dialkyl amino radical; provided, however, at least one of $R_1$, $R_2$ and $R_3$ is a hydrocarbyloxy or heteroatom substituted hydrocarbyloxy radical and provided further that when Y is an oxo, X is not amino or a mono or dialkyl amino radical.

22. A compound according to claim 21 wherein in said compound of formula (I) one of $R_1$, $R_2$, or $R_3$ is alkyloxy and the others are hydroxy radicals.

* * * * *

UNITED STATES PATENT AND TRADEMARK OFFICE
CERTIFICATE OF CORRECTION

PATENT NO. : 5,906,989

DATED : May 26, 1998

INVENTOR(S) : Robert M. Burk

Page 1 of 2

It is certified that error appears in the above-indentified patent and that said Letters Patent is hereby corrected as shown below:

Col. 6, line 40; delete "2" and insert in place thereof --2β--
Col. 6, line 46; after "3α" insert -- - --
Col. 6, line 47; after "2β" insert -- - --
Col. 6, line 53; after "hydroxy" insert -- - --
Col. 7, line 8; delete "3β" and insert in place thereof --3α--
Col. 7, line 19; after "3α" insert -- - --
Col. 7, line 49; after "2β" insert -- - --
Col. 7, line 53; delete "2α" and insert in place thereof --2β--
Col. 7, line 16; after "5" insert -- - --
Col. 9, line 34; after "3α" insert -- - -- (first occurrence)
Col. 10, line 11; after "2β" insert -- - --
Col. 10, line 42; after "3α" insert -- - --
Col. 10, line 60; after "3α" insert -- - --
Col. 11, line 12; delete "THY" and insert in place thereof --THF--
Col. 11, line 39; after "Hydroxy" insert -- - --
Col. 11, line 40; delete "0.052" and insert in place thereof --0.0529--
Col. 11, line 60; after "3α" (first occurrence) and insert -- - --

UNITED STATES PATENT AND TRADEMARK OFFICE
CERTIFICATE OF CORRECTION

PATENT NO. : 5,906,989
DATED : May 26, 1998
INVENTOR(S) : Robert M. Burk

It is certified that error appears in the above-indentified patent and that said Letters Patent is hereby corrected as shown below:

Col. 12, line 56; after "3$\alpha$" (second occurrence) insert -- - --
Col. 13, line 26; delete "THT" and insert in place thereof -- THF--
Col. 13, line 46; after "2$\beta$" insert -- - --
Col. 14, line 19; after "2$\beta$" insert -- - --
Col. 14, line 26; after "3$\alpha$" (second occurrence) insert -- - --
Col. 14, line 64; after "5" insert -- - --
Col. 15, line 1; after "20" insert -- - --
Col. 15, line 10; delete "2$\beta$" (second occurrence)
Col. 16, line 6; delete " 20 to 2" and insert in place thereof --20 to 1--

Signed and Sealed this

Twenty-second Day of May, 2001

Attest:

NICHOLAS P. GODICI

Attesting Officer

Acting Director of the United States Patent and Trademark Office